(12) United States Patent
Wakita et al.

(10) Patent No.: US 7,932,412 B2
(45) Date of Patent: Apr. 26, 2011

(54) METHOD OF MANUFACTURING AN AMINOARYL-CONTAINING ORGANOSILICON COMPOUND AND METHOD OF MANUFACTURING AN INTERMEDIATE PRODUCT OF THE AFOREMENTIONED COMPOUND

(75) Inventors: Keiji Wakita, Midland, MI (US); Yasushi Sugiura, Ichihara (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 12/913,705

(22) Filed: Oct. 27, 2010

(65) Prior Publication Data

US 2011/0040114 A1 Feb. 17, 2011

Related U.S. Application Data

(62) Division of application No. 11/576,571, filed as application No. PCT/JP2005/018723 on Oct. 4, 2005, now Pat. No. 7,847,116.

(30) Foreign Application Priority Data

Oct. 4, 2004 (JP) ................................ 2004-291548

(51) Int. Cl.
*C07F 7/10* (2006.01)
(52) U.S. Cl. ................... 556/409; 556/406; 556/407
(58) Field of Classification Search .................. 556/409, 556/406, 407
See application file for complete search history.

(56) References Cited

U.S. PATENT DOCUMENTS

| | | | |
|---|---|---|---|
| 5,021,585 | A | 6/1991 | Dougherty et al. |
| 5,075,475 | A | 12/1991 | Dougherty et al. |
| 5,081,201 | A | 1/1992 | Dougherty et al. |
| 5,206,328 | A | 4/1993 | Okamura et al. |
| 5,286,890 | A | 2/1994 | Dougherty |
| 2002/0156187 | A1 | 10/2002 | Greene |
| 2003/0162929 | A1 | 8/2003 | Verbruggen et al. |

FOREIGN PATENT DOCUMENTS

| | | |
|---|---|---|
| EP | 0460589 A1 | 12/1991 |
| JP | 08-099979 | 4/1996 |
| JP | 10-036511 | 2/1998 |
| JP | 2000-017176 | 1/2000 |

OTHER PUBLICATIONS

PCT/JP2005/018404 International Search Report, Dec. 22, 2005, 4 pages.
English language translation and abstract for JP 08-099979, 18 pages, Jan. 9, 2008.
English language translation and abstract for JP 2000-017176, 14 pages, Jan. 9, 2008.
English language translation and abstract for JP 10-036511, 18 pages, Jan. 9, 2008.
Craig M Whitaker et al., "Synthesis and Solid-State Structure of Substituted Arylphospine Oxides", J. Org. Chem. 1995, 60, 3499-3508.
Kevin C. Grega et al., "Regioselective Metalation of Fluoroanilines, An Application to the Synthesis of Fluorinated Oxazolidinone Antibacterial Agents", J. Org. Chem, 1995, 60, 5255-5261.
Stevan Djuric et al., "Silicon in Synthesis: Stabase Adducts—A New Primary Amine Protecting Group: Alkylation of Ethyl Glycinate", Tetrahedron Letters, vol. 22, No. 19, pp. 1787-1790, 1981.
R. B. Weisenfeld et al., "Protection of a 2,6-Dialkylaniline: Synthesis of 4-Dimethylmethyoxysilyl-2, 6-Diethylaniline", Synthetic Commmunications, 16(7), 809-817 (1986).
Amy S. Manoso et al., "Improved Synthesis of Aryltriethoxysilanes via Palladium(0)-Catalyzed Silylation of Aryl Iodides and Bromides with Triethoxysilane", J. Org. Chem. 2001, 66, 7449-7455.
Thomas I. Guggenheim, Protection of Substituted Anilines With 1,1,4,4-Tetramethyl-1,4-Bis(N,N-Dimethylamino) Disilethylene, Tetrahedron Letters, vol. 25, No. 12, pp. 1253-1254, 1984.
A.P. Davis et al., "The "Benzostabase" Protecting Group for Primary Amines; Application to Aromatic Amines", Tetrahendron Letters, vol. 31, No. 46, pp. 6721-6724, 1990.
Robert B. Weisenfeld, "Synthesis of Disiloxanediyl Diamines via a Facile Homocondensation of Amino Silanols", J. Org. Chem. 1986, 51, 2434-2436.

*Primary Examiner* — Elvis O Price
(74) *Attorney, Agent, or Firm* — Howard & Howard Attorneys PLLC

(57) ABSTRACT

To provide an aminoaryl-containing organosilicon compound with high efficiency, after protecting amino groups of a haloaniline compound with a specific compound, to form a Grignard reagent and to deprotect the aforementioned groups by reacting the Grignard reagent with a silicon compound.

16 Claims, No Drawings

METHOD OF MANUFACTURING AN AMINOARYL-CONTAINING ORGANOSILICON COMPOUND AND METHOD OF MANUFACTURING AN INTERMEDIATE PRODUCT OF THE AFOREMENTIONED COMPOUND

CROSS-REFERENCE TO RELATED APPLICATIONS

This present application is a divisional of Ser. No. 11/576,571, which was filed on Apr. 3, 2007, which claims priority to and all the advantages of International Patent Application No. PCT/JP2005/018723, filed on Oct. 4, 2005, which claims priority to Japanese Patent Application No. JP 2004-291548, filed Oct. 4, 2004.

TECHNICAL FIELD

The present invention relates to a novel method of manufacturing an aminoaryl-containing organosilicon compound and to a method of manufacturing an intermediate product of the aforementioned compound.

BACKGROUND ART

Organosilicon compounds having aminoaryl groups are know per se, and examples of several methods suitable for synthesis of these compounds have been published. For example, *Journal of Organic Chemistry*, No. 51, page 2434 (1986) discloses a method of synthesis of a p-dimethylmethoxysilylaniline or p-methylmethoxyphenylsilylaniline by preparing a Grignard reagent from an N,N-bis(trimethylsilyl)-p-bromoaniline and deprotecting [the obtained product] with methanol after reaction with a dimethyldichlorosilane or diphenyldichlorosilane. In this example, however, a Grignard reagent is used also for synthesis of the N,N-bis(trimethylsilyl)-p-bromoaniline, and since the low-efficient Grignard reaction has to be repeated twice, the aforementioned method is not suitable for commercial use.

On the other hand, practical examples of Japanese Patent Application Publication (hereinafter Kokai) H8-99979 disclose a specific method of synthesis of N,N-bis(trimethylsilyl) bromoaniline for use as a starting material. However, this method is based on the use of N-trimethylsilyldiethylamine which is a readily available material. Alternatively, the method requires specific synthesis of N-trimethylsilyl-p-bromoaniline which is not easy to perform.

Furthermore, *Synthetic Communication*, No. 16, p. 809 (1986) discloses a method of synthesis of 4-dimethylmethoxysilyl-2,6-diethylaniline. This method, however, cannot be implemented on an industrial scale since it utilizes an organic lithium agent that is even less efficient than the Grignard reagent and therefore requires that the synthesis reaction be conducted in two stages.

*Journal of Organic Chemistry*, No. 66, p. 7449 (2001) discloses a coupling reaction that is conducted between a p-iodoaniline and a trimethoxysilane in the presence of a catalyst. This method is rather impractical for industrial application since it requires the use of a large mount of an expensive palladium catalyst.

DISCLOSURE OF INVENTION

Based on the above description of the state of the art, the present invention is aimed at providing an efficient method for manufacturing an aminoaryl-containing organosilicon compound without the use of an organic lithium agent having low efficiency or an expensive palladium agent and at performing the aforementioned method in a single Grignard reaction. It is another object to provide an intermediate product of the aforementioned organosilicon compound.

The inventors herein have conducted a profound study aimed at achieving the above objects. Based on the results of this study, it has been found that an aminoaryl-containing organosilicon compound can be synthesized by:
causing a reaction between a compound of general formula (2):

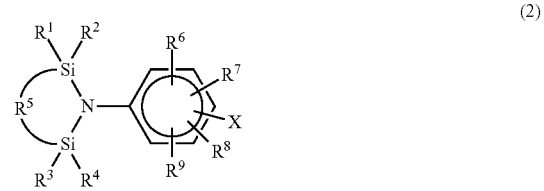

(2)

(where $R^1$, $R^2$, $R^3$, and $R^4$ are independently alkyl groups with 1 to 4 carbon atoms, $R^5$ is an oxygen atom or an alkylene group with 1 to 6 carbon atoms, and $R^6$, $R^7$, $R^8$, and $R^9$ independently represent a hydrogen atom, an alkyl group with 1 to 4 carbon atoms, or an alkoxy group with 1 to 4 carbon atoms; and X is a halogen atom) and an active metal or a metalloorganic compound of general formula (3):

(3)

(where $R^{11}$ is a univalent hydrocarbon group, M is a bivalent metal, X is a halogen atom), thus preparing a Grignard compound of general formula (4):

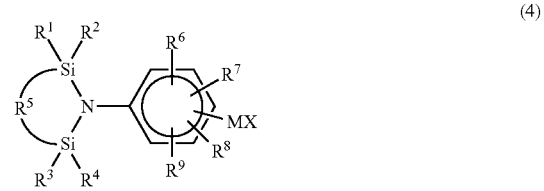

(4)

(where $R^1$, $R^2$, $R^3$, $R^4$, $R^5$, $R^6$, $R^7$, $R^8$, $R^9$, M, and X are the same as defined above);
causing a reaction between the obtained Grignard compound and an organosilicon compound of general formula (5):

(5)

(where Y, $R^{10}$, and n are the same as defined above), thus obtaining an organosilicon compound of general formula (1):

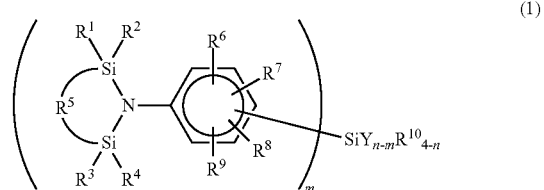

(1)

(where $R^1$, $R^2$, $R^3$, $R^4$, $R^5$, $R^6$, $R^7$, $R^8$, $R^9$, $R^{10}$ Y, n are the same as defined above, and m is an integer between 1 and n);

deprotecting the obtained organosilicon compound; and then obtaining the target compound of general formula (6):
[Sixth Chemical Formula]

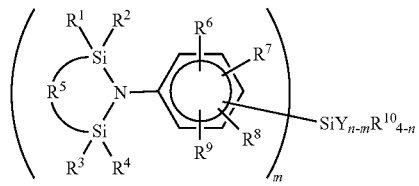

(where $R^6, R^7, R^8, R^9, R^{10}, Y, n$, and $m$ are the same as defined above) in a single-stage Grignard reaction. Thus the authors arrived at the present invention.

The aforementioned compound of general formula (2) can be produced by causing a reaction between a compound represented by general formula (7):

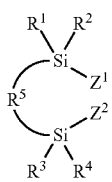

(where $R^1, R^2, R^3$, and $R^4$ are independently alkyl groups with 1 to 4 carbon atoms, $R^5$ is an oxygen atom or an alkylene group with 1 to 6 carbon atoms, and $Z^1$ and $Z^2$ independently represent halogen atoms) and a compound represented by general formula (8):

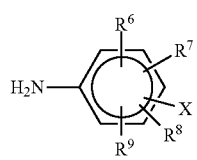

(where $R^6, R^7, R^8$, and $R^9$ independently represent a hydrogen atom, an alkyl group with 1 to 4 carbon atoms, or an alkoxy group with 1 to 4 carbon atoms; and X is a halogen atom), the reaction being carried out under basic conditions and in the absence of an organic metal compound.

EFFECTS OF THE INVENTION

Aminoaryl-containing organosilicon compounds are suitable for use as a starting material for polyimide resin, polyimide silicone resin, etc. Since such compounds have higher thermal stability than conventional aminoalkyl-containing organosilicon compounds, they are suitable for use as silane coupling agents for high-temperature applications. The effect of the invention consists of providing such aminoaryl-containing organosilicon compounds that can be synthesized with high production efficiency.

BEST MODE FOR CARRYING OUT THE INVENTION

The present invention allows synthesis of an aminoaryl-containing organosilicon compound in the following three steps:

1. Synthesis of the compound of general formula (2);
2. Synthesis of an organosilicon compound of general formula (1) from a compound of general formula (2) by a Grignard reaction; and
3. Deprotection of the organosilicon compound of general formula (1).

Each of these steps will now be considered separately.
<Step 1>
According to the invention, the silyl-protected haloaniline compound of general formula (2):

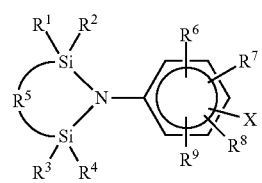

(where $R^1$, $R^2$, $R^3$, and $R^4$ independently represent alkyl groups with 1 to 4 carbon atoms;
$R^5$ represents an oxygen atom or an alkylene group with 1 to 6 carbon atoms;
$R^6, R^7, R^8$, and $R^9$ independently represent a hydrogen atom, an alkyl group with 1 to 4 carbon atoms, or an alkoxy group with 1 to 4 carbon atoms; and X represents a halogen atom) is used as an intermediate product for synthesis of the aminoaryl-containing organosilicon compound of general formula (6).

The alkyl groups with 1 to 4 carbon atoms may be represented by a methyl group, ethyl group, propyl group, isopropyl group, butyl group, iso-butyl group, sec-butyl group, and tert-butyl group. The methyl group is preferable.

The alkoxy groups with 1 to 4 carbon atoms may be represented by a methoxy group, ethoxy group, propoxy group, isopropoxy group, butoxy group, iso-butoxy group, sec-butoxy group, and tert-butoxy group, of which the methoxy group or the ethoxy group is preferable.

The alkylene group with 1 to 6 carbon atoms can be represented by a methylene group, ethylene group, propylene group, isopropylene (—$CH_2$—$CH(CH_3)$—) group, butylenes group, iso-butylene (—$CH_2$—$CH(CH_3)$—$CH_2$—) group, sec-butylene ($CH(CH_3)$—$CH_2$—$CH_2$—), and tert-butylene (—$CH_2$—$C(CH_3)_2$—). The methylene and ethylene groups are preferable. Most preferable is the ethylene group.

The halogen atom can be represented by a fluorine atom, chlorine atom, bromine atom, or iodine atom. of which chlorine or bromine atom, and especially chlorine atom is preferable.

The compound of general formula (2) can be easily synthesized by causing a reaction between the compound of general formula (7):

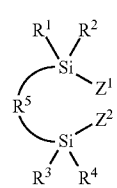

(where $R^1$, $R^2$, $R^3$, and $R^4$ are independently alkyl groups with 1 to 4 carbon atoms, $R^5$ is an oxygen atom or an alkylene group with 1 to 6 carbon atoms, and $Z^1$ and $Z^2$ independently represent halogen atoms) and a compound represented by general formula (8):

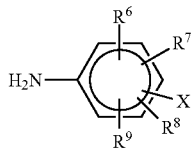
(8)

(where $R^6$, $R^7$, $R^8$, and $R^9$ independently represent a hydrogen atom, an alkyl group with 1 to 4 carbon atoms, or an alkoxy group with 1 to 4 carbon atoms; and X is a halogen atom), the reaction being carried out under basic conditions and without the presence of an organic metal compound.

The compound of general formula (7) can be exemplified, e.g., by 1,3-dichloro-1,1,3,3-tetraisopropyldisiloxane, 1,2-bis(chlorodimethylsilyl)ethane, etc.

The compound of general formula (8) can be represented by m-chloroaniline, p-chloroaniline, m-bromoaniline, p-bromoaniline, 2,6-diethyl-4-bromoaniline, etc.

The aforementioned basic conditions are achieved without an organic metal compound but with the use of a sodium carbonate, or other inorganic basic compounds, or with the use of amines, or other organic basic compounds. The use of organic basic compounds is preferable. Examples of such organic basic compounds are the following: triethylamine, picoline, 1,8-diazabicyclo[5.4.0]undeca-7-ene, or similar aliphatic amines, aromatic amines, or cyclic amines. Triethylamine, or similar tertiary aliphatic amines are most preferable from the point of view of reactivity with respect to the compound of general formula (7).

The compound of general formula (7) is available on the market in the form of several reagents, each of which can be used for the purposes of the invention. If necessary, however, this compound can be synthesized by a known reaction between simple compounds. For example, 1,2-bis(chlorodimethylsilyl)ethane can be easily synthesized by means of a hydrosilation reaction between a chlorodimethylvinylsilane and chlorodimethylsilane.

The compound of general formula (8) is readily available since it is commercially produced in the form of several reagents.

The reaction between the compounds of general formulae (7) and (8) can be easily performed, e.g., by mixing these compounds in the presence of the aforementioned basic compound, but to avoid intense reaction, it is recommended to add one of the compounds dropwise to a system that contains the other compound. A reaction between both compounds creates a salt of the aforementioned basic compound.

The reaction can be carried out at a temperature within the range of 0 to 120° C., preferably between room temperature and 80° C.

A solvent is not an indispensable component of the aforementioned reaction, but for improving stirring conditions during the reaction, a solvent that is inert with respect to the compounds (7) and (8) can be used. Examples of such solvent are toluene, xylene, heptane, etc.

Upon completion of the reaction between compounds (7) and (8), compound of formula (2) can be separated from the reaction product by filtering or washing out the basic compound salt. The obtained compound of general formula (2) can be further subjected to purification via distillation or another process for increasing the yield of the reaction that will be described later.

<Step 2>

In the next step, the compound of general formula (2) is converted into a Grignard reagent. The Grignard reagent of the compound of formula (2) can be easily synthesized by a conventional Grignard preparation method. In accordance with the invention, the compound of general formula (2) is caused to react with an active metal or an organic metal compound of general formula (3):

$$R^{11}MX \qquad (3)$$

(where $R^{11}$ is a univalent hydrocarbon group, M is a bivalent metal, and X is a halogen atom), whereby a Grignard reagent of general formula (4) is produced:

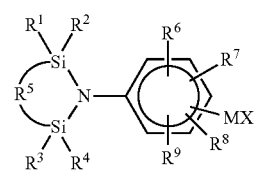
(4)

(where $R^1$, $R^2$, $R^3$, $R^4$, $R^5$, $R^6$, $R^7$, $R^8$, $R^9$, M, and X are the same as defined above).

The univalent hydrocarbon group can be represented by a univalent saturated hydrocarbon group having 1 to 10, preferably 1 to 6, and even more preferably, 1 or 2 carbon atoms, or by a univalent unsaturated hydrocarbon group having 2 to 10, preferably 2 to 8 or 2 to 6, and even more preferably, 2 to 4 carbon atoms.

The aforementioned univalent saturated hydrocarbon group having 1 to 10 carbon atoms can be exemplified by a methyl group, ethyl group, n-propyl group, isopropyl group, n-butyl group, isobutyl group, sec-butyl group, tert-butyl group, pentyl group, hexyl group, heptyl group, octyl group, nonyl group, decyl group, or other alkyl groups.

The aforementioned unsaturated hydrocarbon groups with 2 to 10 carbon atoms can be divided into unsaturated aliphatic hydrocarbon groups with 2 to 10 carbon atoms and aromatic hydrocarbon groups with 6 to 10 carbon atoms. The unsaturated aliphatic hydrocarbon groups with 2 to 10 carbon atoms can be exemplified by a vinyl group, 1-propenyl group, allyl group, isopropenyl group, 1-butenyl group, 2-butenyl group, or similar alkenyl groups. The vinyl group is preferable from the point of view of cross-linking reactivity of the polysiloxane. The aromatic hydrocarbon group with 6 to 10 carbon atoms can be represented by a phenyl group, tolyl group, xylyl group, etc.

Among all univalent hydrocarbon groups, most preferable is the alkyl group with 1 to 10 carbon atoms, especially, the methyl group.

The bivalent metal atoms along with active metals can be represented by alkali earth metals or zinc group metals, especially magnesium or zinc.

It is recommended to carry out the reaction between the compound of general formula (2) and the active metal or the organic metal compound of general formula (3) in the presence of an ether-type solvent. For example, the Grignard reagent of general formula (4) can be easily prepared by gradually adding an ether solution of the compound of formula (2) in a dropwise manner to the organic metal compound of general formula (3) or the active metal in an ether solvent.

The aforementioned ether solvent may be exemplified by diethyl ether, tetrahydrofuran, bis (2-methoxyethyl)ether, or other ether-type solvent normally used for synthesis of Grignard reagents. Tetrahydrofuran is preferable in view of its high reactivity and low cost.

The reaction can be carried out at a temperature within the range of 0° C. to the boiling point of the solvent, but preferably between 50° C. and 80° C.

The obtained Grignard reagent of general formula (4) is then caused to react with a silicon compound of general formula (5):

(where Y is a hydrolysable group, $R^{10}$ is a univalent hydrocarbon group, and n is an integer between 1 and 4), whereby an organosilicon compound of general formula (1):

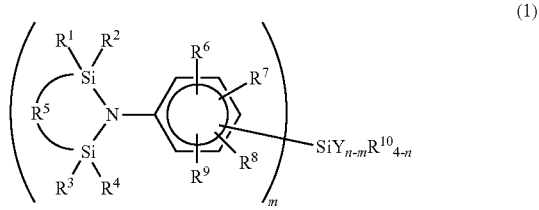

(where,
$R^1$, $R^2$, $R^3$, and $R^4$ independently represent alkyl groups with 1 to 4 carbon atoms;
$R^5$ represents an oxygen atom or an alkylene group with 1 to 6 carbon atoms;
$R^6$, $R^7$, $R^8$, and $R^9$ independently represent a hydrogen atom, an alkyl group with 1 to 4 carbon atoms, or an alkoxy group with 1 to 4 carbon atoms;
$R^{10}$ represents a univalent hydrocarbon group;
Y represents a hydrolysable group;
n is an integer from 1 to 4; and
m is an integer between 1 and n) is synthesized. The organosilicon compound of general formula (1) comprises a second intermediate product used in the synthesis of the aminoaryl-containing organosilicon compound of general formula (6).

The hydrolysable group can be exemplified by an arbitrary hydrolysable group, but preferable are halogen atoms and alkoxy groups with 1 to 4 carbon atoms, especially, chlorine atoms, methoxy groups, and ethoxy groups.

The following are specific examples of silicon compounds of general formula (5): chlorotrimethylsilane, dimethyldichlorosilane, tetrachlorosilane, methoxytrimethylsilane, dimethoxydimethylsilane, methyltrimethoxysilane, tetramethoxysilane, tetraethoxysilane, etc.

Equivalent relationships in the reaction between the Grignard reagent of general formula (4) and the silicon compound of formula (5) can be arbitrary, and the appropriate equivalent quantities are selected with reference to the required values of "m" and "n". For example, when it is necessary to obtain an organosilicon compound with n>1 and m=1, it is recommended, for an increase in the product yield, to use the silicon compound of general formula (5) in an excess of the Grignard reagent of general formula (4) by 2 to 5 equivalent amounts. On the other hand, when it is necessary to obtain the organosilicon compound with n=m, the Grignard reagent of general formula (4) should be used either in the same equivalent amount as the silicon compound of general formula (5) or in a small excess over the silicon compound.

Normally, the aforementioned reaction is carried out either with dropwise addition of the silicon compound of formula (5) to the Grignard reagent of formula (4), or, vice verse, with dropwise addition of the Grignard reagent of formula (4) to the silicon compound of formula (5).

When in the above reaction the Grignard reagent of formula (4) is prepared with participation of a solvent, this solvent can be used as a continuous reaction solvent. Furthermore, if necessary, a solvent inert to the reagents, such as toluene, xylene, heptane, tetrahydrofuran, etc., can be added to the reaction system.

It is recommended to conduct the last mentioned reaction at a temperature within the range of −20° C. to 80° C., preferably at a temperature between 0° C. and 20° C.

Upon completion of the above reaction, the organosilicon compound of formula (1) is separated by removing the salt formed in the reaction by filtering or washing, and, if necessary, the solvent is removed by distillation. Alternatively, the reaction mixture can be used for the next step as it is, i.e., without separation operations.

<Step 3>

The organosilicon compound of general formula (1) is subjected to a deprotection reaction and is turned into an aminoaryl-containing organo silicon compound of general formula (6):

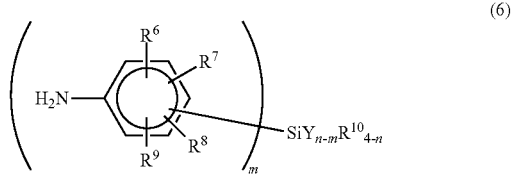

(where $R^6$, $R^7$, $R^8$, and $R^9$ independently represent a hydrogen atom, an alkyl group with 1 to 4 carbon atoms, or an alkoxy group with 1 to 4 carbon atoms;
$R^{10}$ represents a univalent hydrocarbon group;
Y represents a hydrolysable group;
n is an integer from 1 to 4; and
m is an integer between 1 and n).

The deprotection reaction is a reaction that is carried out, preferably in the presence of a catalyst, between a compound having an active hydrogen atom and the organosilicon compound of general formula (1).

A catalyst suitable for the aforementioned reaction is a compound that can be used as an acidic or a basic compound. The acidic compound may be represented by a mineral acid or its salt, such as a hydrochloric acid, sulfuric acid, ammonium chloride, etc. The basic compound can be exemplified by a metal hydroxide or alkoxide, such as sodium hydroxide, potassium hydroxide, sodium methoxide, or the like. In some cases, when impurities or by-products present in the reaction system may function as catalysts, the reaction may be carried out without addition of a catalyst.

From the view point of improved reactivity to the organosilicon compound of general formula (1), it is recommended that the aforementioned compound with active hydrogen comprises one with a hydroxyl group. Examples of such compounds are water, methanol, ethanol, and the like.

It is recommended that deprotection be carried out at a temperature close to room temperature, but if necessary, the deprotection reaction can be carried out with heating. The reaction may be carried out without the presence of a solvent in the reaction system. If necessary, however, a solvent, neutral to the reagents of the reaction, such as toluene, xylene, heptene, tetrahydrofuran, etc. can be present.

Upon completion of the deprotection reaction, the aminoaryl-containing organosilicon compound of general formula (6) can be purified to a sufficient purity by removing by-products via stripping. If necessary, further purification can be conducted by distillation or by other means.

A product of hydrolyzation of the aminoaryl-containing organosilicon compound of general formula (6) can be obtained by reacting the aminoaryl-containing organosilicon compound of general formula (6) with water as a compound that contains active hydrogen. In case the active-hydrogen containing compound is water, the deprotection reaction can be carried out simultaneously with the hydrolyzation reaction, whereby synthesis of a product of hydrolysis of the aminoaryl-containing organosilicon compound of general formula (6) can be simplified.

The following are examples of the aforementioned aminoaryl-containing organosilicon compounds of general formula (6) and products of the hydrolyzation: p-aminophenyl-trimethylsilane, bis (p-aminophenyl) dimethylsilane, p-aminophenyl-trimethoxysilane, bis (p-aminophenyl) dimethoxysilane, p-aminophenyl-dimethylmethoxysilane, p-aminophenyl-triethoxysilane, 1,3-bis(p-aminophenyl) 1,1,3,3-tetramethylsiloxane, m-aminophenyltrimethylsilane, m-aminophenyltrimethoxysilane, o-aminophenyl-trimethylsilane, o-aminophenyltrimethoxysilane, (4-amino-3,5-diethylphenyl)trimethylsilane, etc.

PRACTICAL EXAMPLES

The invention will be further described in more detail with reference to practical examples, which, however, should not be construed as limiting the scope of application of the invention.

Practical Example 1

A 1-liter four-neck flask equipped with a thermometer, stirrer, and a refluxing cooler was loaded with 63.8 g (0.5 mole) of p-chloroaniline, 111.3 g (1.1 mole) of triethylamine, and toluene (200 g). While the components were stirred, a solution of 107.6 g (0.5 mole) of 1,2-bis(chlorodimethylsilyl)ethane in 60 g of toluene were added dropwise. The reaction heat raised the temperature in the system from room temperature to 45° C. After the reaction mixture was aged by hot refluxing for 2 hours at 110° C., it was cooled to room temperature, the salt was removed by filtering, and after the solvent was removed by distillation in vacuum, a compound of general formula (1):

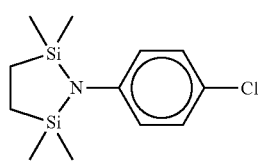

(I)

was produced with a yield of 89%.

Practical Example 2

A 300-milliliter four-neck flask equipped with a thermometer, stirrer, and a refluxing cooler was loaded with 5.35 g (0.22 mole) of magnesium and 54 g of tetrahydrofuran, and then the content was activated by adding 1.85 g (0.02 mole) of t-butyl chloride, while the components were stirred in a nitrogen flow.

An appropriate Grignard reagent was prepared by adding a solution of 54.0 g (0.2 mole) of the compound of the aforementioned formula obtained in Practical Example 1 in 54 g of tetrahydrofuran. The solution was added dropwise at 55° C. The obtained Grignard reagent solution was added dropwise to a solution of 21.7 g (0.2 mole) of chlorotrimethylsilane in 30 g of tetrahydrofuran. The salt formed in the reaction was removed by filtering, and a deprotection reaction was carried out by adding 50 g of methanol. Sodium methoxide was added until the liquid became neutral, the solvent was removed by distillation, and the product was again distilled in vacuum to produce a p-aminophenyltrimethoxysilane with a yield of 62%.

Practical Example 3

A compound of formula (II):

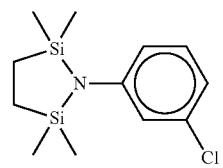

(II)

was produced with a yield of 79% in the same manner as in Practical Example 1, except that m-chloroaniline was used instead of the p-chloroaniline.

Practical Example 4

A 300-milliliter four-neck flask equipped with a thermometer, stirrer, and a refluxing cooler was loaded with 5.35 g (0.22 mole) of magnesium and 54 g of tetrahydrofuran, and then the content was activated by adding 3.76 g (0.02 mole) of 1,2-dibromoethane, while the components were stirred in a nitrogen flow.

An appropriate Grignard reagent was prepared by adding a solution of 54.0 g (0.2 mole) of the compound of the aforementioned formula obtained in Practical Example 3 in 54 g of tetrahydrofuran. The solution was added dropwise at 55° C. The obtained Grignard reagent solution was added dropwise to 91.3 g (0.6 mole) of tetramethoxysilane. The salt formed in the reaction was removed by filtering, and after distillation in vacuum, a compound of formula (III):

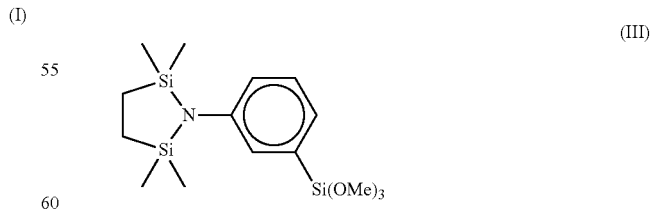

(III)

was produced with a yield of 54%.

Practical Example 5

A 100-milliliter three-neck flask equipped with a thermometer, stirrer, and a refluxing cooler was loaded with 33.8 g (0.95 mole) of the compound of the aforementioned formula obtained in Practical Example 4 and 35 g of tetrahydrofuran. Methanol (15 g) was then added dropwise. The reaction heat raised the temperature of the system from room temperature to 48° C. After the solvent was removed by distillation, the product was distilled in vacuum to produce m-aminophenyl trimethoxysilane with a yield of 96%.

Practical Example 6

An appropriate Grignard reagent corresponding to the compound of formula (II) was prepared by the same method as in Practical Example 4. The obtained Grignard reagent was added dropwise to 72.1 g (0.6 mole) of a dimethoxydimethylsilane. The salt formed in the process was removed by filtering, and the product was distilled in vacuum to produce a compound of formula (IV):

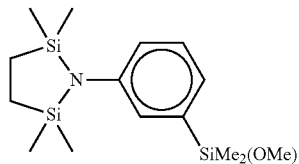

(IV)

with the yield of 58%.

Practical Example 7

A 100-milliliter three-neck flask equipped with a thermometer, stirrer, and a refluxing cooler was loaded with 40.7 g (0.126 mole) of the compound of aforementioned formula (IV). Methanol (10 g) was then added dropwise. The reaction heat raised the temperature of the system from room temperature to 65° C. After the residual methanol was removed by distillation, the product was distilled in vacuum to produce m-aminophenyl dimethylmethoxysilane with a yield of 96%. The obtained product was hydrolyzed, whereby an oil having 1,3-bis(m-aminophenyl)-1.1.3.3-tetramethyldisiloxane as a main component was obtained.

The invention claimed is:

1. A method of manufacturing an aminoaryl-containing organosilicon compound represented by general formula (6):

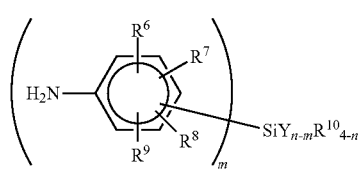

(6)

(where $R^6$, $R^7$, $R^8$, $R^9$, $R^{10}$, Y, n, and m are the same as defined below) by subjecting an organosilicon compound of general formula (1):

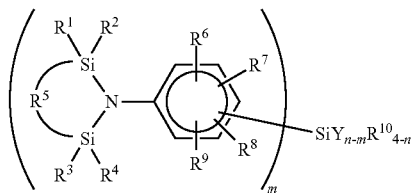

(1)

where
$R^1$, $R^2$, $R^3$, and $R^4$ independently represent alkyl groups with 1 to 4 carbon atoms;
$R^5$ represents an alkylene group with 1 to 6 carbon atoms;
$R^6$, $R^7$, $R^8$, and $R^9$ independently represent a hydrogen atom, an alkyl group with 1 to 4 carbon atoms, or an alkoxy group with 1 to 4 carbon atoms;
$R^{10}$ represents a univalent hydrocarbon group;
Y represents a hydrolysable group;
n is an integer from 1 to 4; and
m is an integer from 1 to n,
to a deprotection reaction.

2. A method as set forth in claim 1 wherein $R^5$ represents an ethylene group.

3. A method as set forth in claim 1 wherein m is 1 and n is greater than 1.

4. A method as set forth in claim 1 wherein m is equal to n.

5. A method as set forth in claim 1 wherein the deprotection reaction is carried out between a compound having an active hydrogen atom and the organosilicon compound of general formula (1).

6. A method as set forth in claim 5 wherein the deprotection reaction is carried out in the presence of a catalyst.

7. A method as set forth in claim 6 wherein the catalyst is an acidic compound.

8. A method as set forth in claim 7 wherein the acidic compound is further defined as a mineral acid or its salt.

9. A method as set forth in claim 8 wherein the acidic compound is selected from the group of hydrochloric acid, sulfuric acid, or ammonium chloride.

10. A method as set forth in claim 6 wherein the catalyst is a basic compound.

11. A method as set forth in claim 10 wherein the basic compound is further defined as a metal hydroxide or alkoxide.

12. A method as set forth in claim 11 wherein the basic compound is selected from the group of sodium hydroxide, potassium hydroxide, or sodium methoxide.

13. A method as set forth in claim 5 wherein the compound having the active hydrogen comprises a hydroxyl group.

14. A method as set forth in claim 1 wherein deprotection is carried out without the presence of solvent.

15. A method as set forth in claim 1 further comprising the step of purifying the compound of general formula (6).

16. A method as set forth in claim 15 wherein the compound of general formula (6) is purified via stripping.

* * * * *